(12) United States Patent
Kao et al.

(10) Patent No.: US 6,803,479 B2
(45) Date of Patent: Oct. 12, 2004

(54) REAGENTS AND METHOD FOR SPATIO-TEMPORAL CONTROL OF GENE EXPRESSION BY ILLUMINATION

(75) Inventors: Joseph Pao Yung Kao, Silver Spring, MD (US); David Ari Freilich, Cockeysville, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 308 days.

(21) Appl. No.: 10/078,339

(22) Filed: Feb. 21, 2002

(65) Prior Publication Data

US 2003/0018073 A1 Jan. 23, 2003

Related U.S. Application Data

(60) Provisional application No. 60/270,130, filed on Feb. 22, 2001.

(51) Int. Cl.[7] ............................................. C07C 205/00
(52) U.S. Cl. ............................................. 560/21; 560/22
(58) Field of Search ...................................... 560/21, 22

(56) References Cited

U.S. PATENT DOCUMENTS 4,985,461 A * 1/1991 Hsu et al.

FOREIGN PATENT DOCUMENTS

EP              632016         *    1/1995

OTHER PUBLICATIONS

Monroe et al, *J. of Biol. Chem.*, 274(30):20895–20900.
Cambridge et al, *Science*, 277:825–828 (1997).

* cited by examiner

*Primary Examiner*—Paul J. Killos
(74) *Attorney, Agent, or Firm*—Sughrue Mion, PLLC

(57) ABSTRACT

A caged non-steroidal ecdysome memetic (NSE) compound and a method for producing free NSE by subjecting the charged NSE to UV irradiation.

10 Claims, 7 Drawing Sheets

Figure 1:
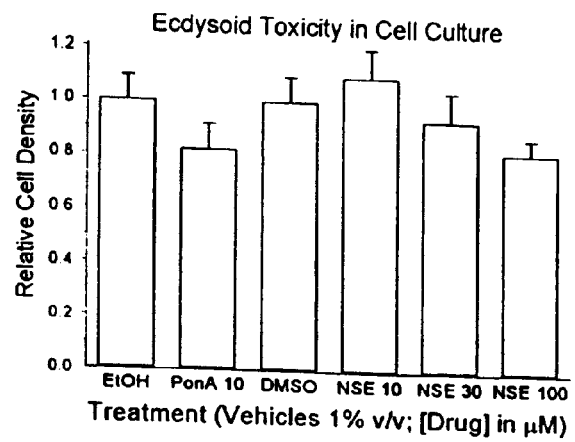

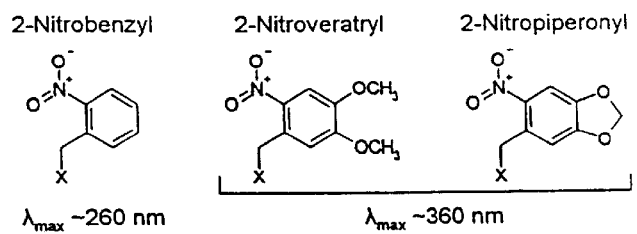
FIGURE 11
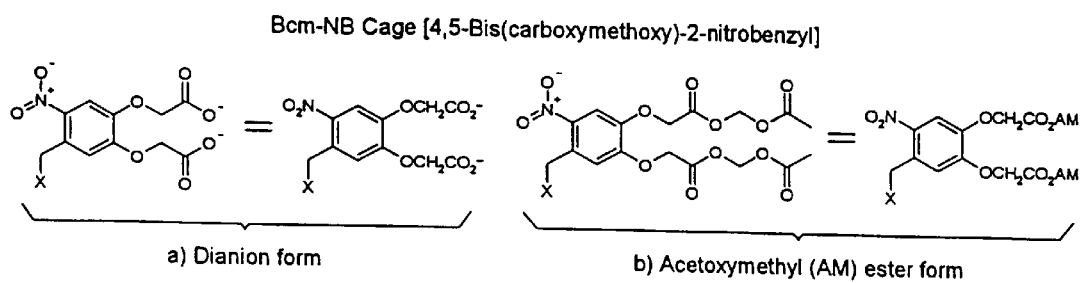
a) Dianion form
b) Acetoxymethyl (AM) ester form
FIGURE 12A
FIGURE 12B

REAGENTS AND METHOD FOR SPATIO-TEMPORAL CONTROL OF GENE EXPRESSION BY ILLUMINATION

This application claims benefit of Provisional Application No. 60/270,130, filed Feb. 22, 2001. The disclosure of which is incorporated herein by reference.

STATEMENT OF INVENTION

This invention is a photosensitive and photolabile precursor of a non-steroidal ecdysone mimetic (NSE), or a "caged" NSE. A caged NSE is biologically inactive until it is photochemically transformed by light to yield free NSE, which is biologically active. A caged NSE can be introduced into living cells and tissues having the appropriate protein machinery and genes under ecdysone promoter control. When illuminated, biologically active NSE will be generated photochemically in situ, and activate expression of the genes placed under ecdysone promoter regulation. Caged NSE thus allows the researcher to turn on recombinant gene expression with unprecedented spatial and temporal control.

BACKGROUND INFORMATION ON THE CHEMICAL STRUCTURES ON WHICH THIS INVENTION IS BASED

NSEs are molecules that act biologically as does the insect hormone ecdysone, which controls the molting process during insect growth and development. NSEs have been put to two uses: 1) as an insecticide against agriculturally damaging insect pests (it acts by disrupting the normal endocrine regulation of insect growth); and 2) as an activator of transgene expression in transgenic cells in which an exogenous gene is placed under transcriptional regulation of the ecdysone promoter. Insecticidal use of the bisacylhydrazine class of NSEs was developed primarily by researchers at Rohm and Haas. The use of one of the bisacylhydrazine NSEs for ecdysone promoter-regulated transgene activation was introduced by Invitrogen (Invitrogen markets a bisacylhydrazine compound under the name "GS-E," under license from Rohn and Haas). The same advantage of NSE underlies both its insecticidal and transgenic gene expression applications. The bisacylhydrazines are non-toxic and environmentally benign, and because they are mechanism-based drugs, work only against certain classes of agricultural pests without affecting other lifeforms. Similarly, because the ecdysone molting hormone system is unique to insects, when the ecdysone promoter system is used to control transgene expression in non-insect organisms, it can be activated only by applying ecdysone steroid or its bioactive mimetics. The NSEs thus afford a non-toxic method for activating transgene expression in organisms other than insects.

SUGGESTED SCOPE OF INVENTION

The primary intended use of caged NSEs is for activating transgene expression with high temporal and spatial resolution in transgenic cells, tissues, or developing animals.

RESULTS DEMONSTRATING THE CONCEPT IS VALID

Caged Molecules Our laboratory has been designing, synthesizing caged molecules, as well as developing their applications in biological systems for over ten years. The concept of using light to rapidly transform a biologically inactive molecule into a biologically active one in situ has been repeatedly proven in a variety of reagents.

Synthesis and Characterization of a NSE, upon which the Caged NSE is Based

We have synthesized and characterized a NSE of the bisacylhydrazine family, namely, 1-(3,5-dimethylbenzoyl)-1-tert-butyl-2-(2-ethyl-3-methoxybenzoyl)hydrazine (hereafter referred to as NSE-1). The chemical synthesis is shown in Schemes 1 and 2. Physical properties are shown in Table 1.

Scheme 1
Synthesis of Non-Steroidal Ecdysoid (NSE)

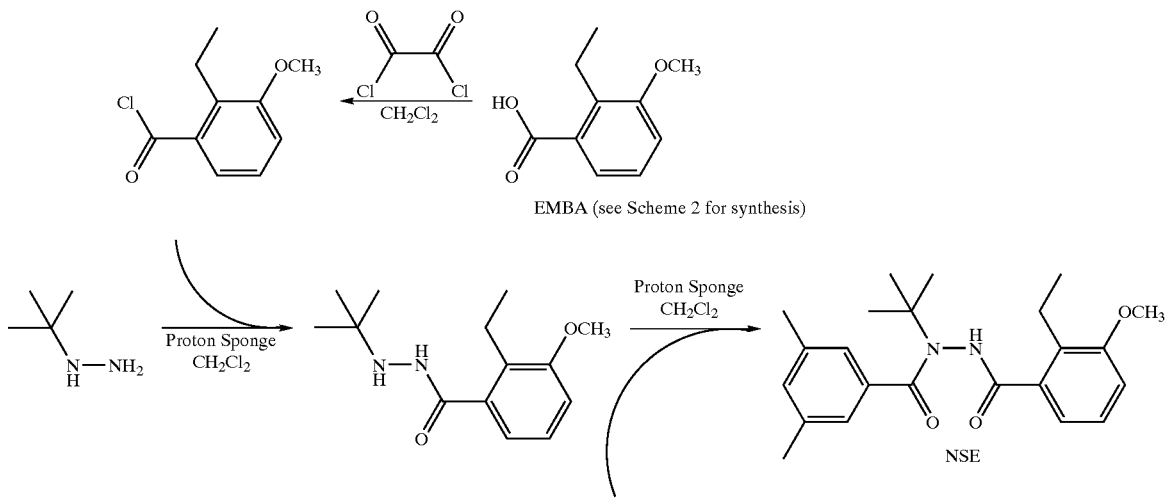

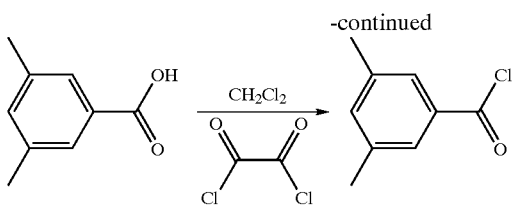

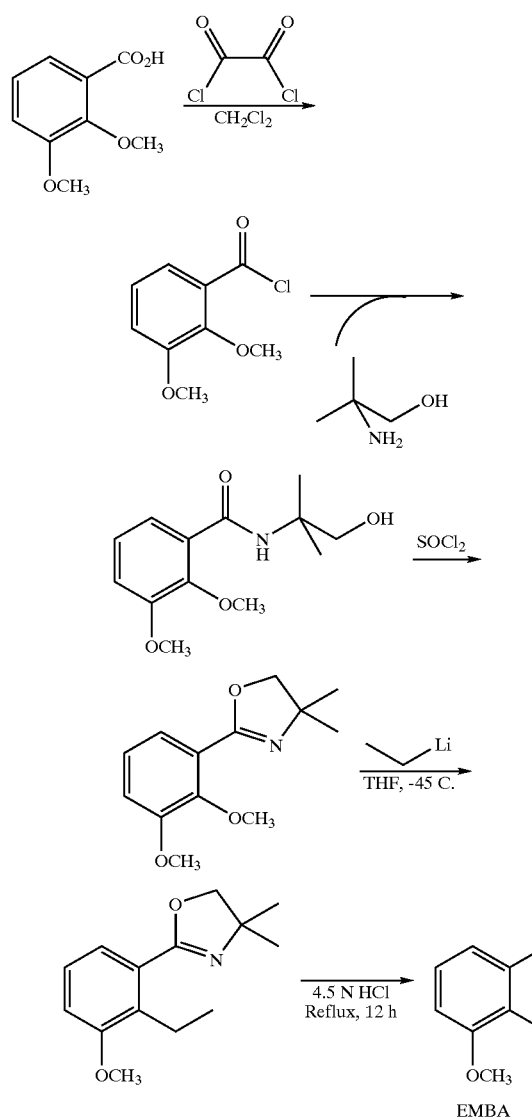

Scheme 2
Synthesis of 2-Ethyl-3-Methoxy-Benzoic Acid (EMBA)

EMBA

TABLE 1

Physical properties of 1-(3,5-dimethylbenzoyl)-1-tert-
butyl-2-(2-ethyl-3-methoxybenzoyl) hydrazine

| Chemical Formula | $C_{23}H_{30}N_2O_3$ |
|---|---|
| Molecular Weight | 382.51 |

TABLE 1-continued

Physical properties of 1-(3,5-dimethylbenzoyl)-1-tert-
butyl-2-(2-ethyl-3-methoxybenzoyl) hydrazine

| Aqueous Solubility* | 47 $\mu$M |
|---|---|
| Extinction Coefficient at 280 nm ($\epsilon_{280}$)* | 2,550 ± 80 L · mol$^{-1}$ · cm$^{-1}$ |

*Measured in 100 mM KCl, 10 mM K · HEPES, pH 7.4

Biological Testing of NSE-1

Toxicity of NSE-1 in Cell Culture

Cellular toxicity of NSE-1 was tested in cell culture. NIH3T3-ER fibroblasts (Stratagene, La Jolla, Calif.) were seeded into 96-well plates, allowed to attach for 24 hours in DMEM supplemented with 10% v/v fetal bovine serium (FBS). The medium was then replaced with DMEM-10 FBS containing ecdysoid drugs or solvent vehicle, and the cells were allowed to grow for 48 hours, at the end of which the cells were lysed and the amount of DNA in each well quantified through the CyQuant assay (Molecular Probes, Inc. Eugene, Oreg.). Neither Ponasterone A at 10 $\mu$M, nor NSE-1 at 10, 30 or 100 $\mu$M significantly affected the growth capacity of the cells. The data are summarized in FIG. 1. These data suggest that NSE-1 is not cytotoxic.

Toxicity of NSE-1 in Animals

NSE-1 was suspended (32.5 mg/ml) in carrier vehicle consisting of 15% w/v Pluronic F127 surfactant (BASF Corp., Wyandotte, Mich.) and 3% v/v dimethylsulfoxide in phosphate buffered saline (PBS, pH 7). Intraperitoneal injections of this formulation (six 200-$\mu$l aliquots administered at 12-hour intervals) into 8 mice did not produce any signs of intoxication. These observations give at least preliminary data showing that NSE-1 is not acutely toxic to mammals.

Induction of Transgene Expression in Transiently-Transfected Cells

Figure 2:
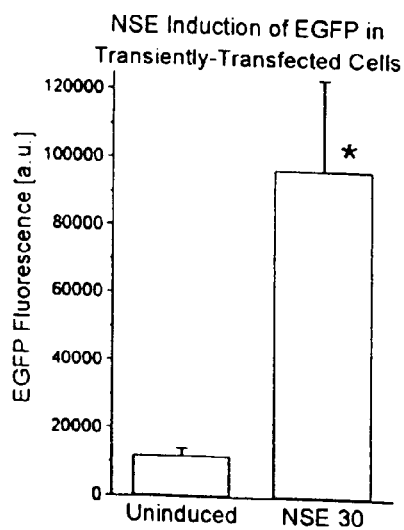

NIH3T3-ER cells were transiently transfected with a plasmid pEGSH-GFP carrying the reporter eGFP gene under ecdysone promoter control. The transfected cells were treated with 10 $\mu$M ponasterone A, or 30 $\mu$M NSE-1, or plain medium for 48 hours and then screened for induction of eGFP expression by single-cell microfluorimetry. The results are shown in FIG. 2. These results demonstrate the efficacy of NSE-1 in inducing transgenes in cultured cell lines.

Chemical Synthesis of New Cage

Synthesis of the photosensitive caging group to be used for the caged NSE invention is nearing completion. The structure of the caging reagent is shown to the right.

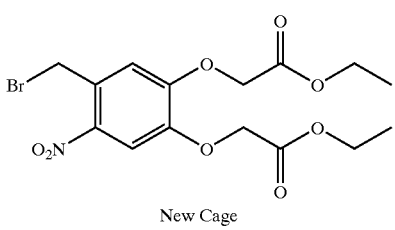

New Cage

Caging Reaction of NSE

We have completed a caging reaction of NSE-1 with a known cage which shares structural features with the proposed new cage shown above. This model reaction is shown in the scheme below. That this model reaction was successful suggests that when the new cage is synthesized, its caging reaction with NSE-1 will mostly likely be successful.

Model reaction for caging NSE

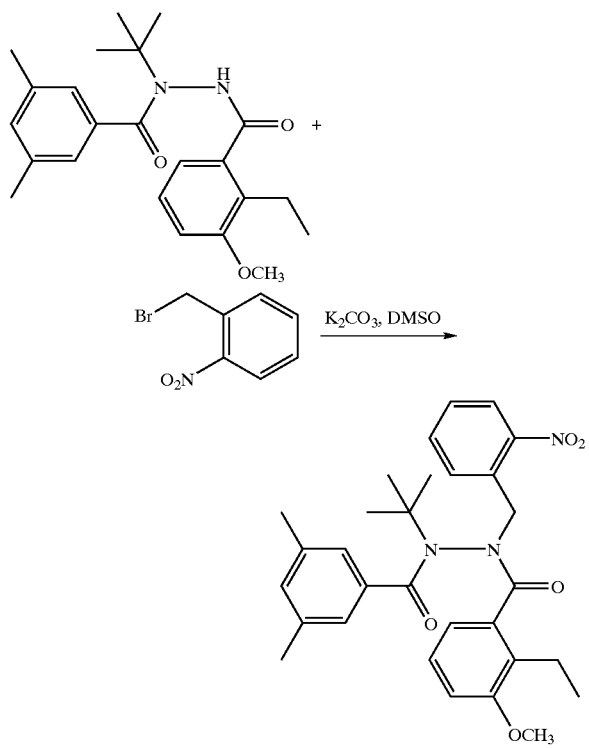

VARIATIONS AND ALTERED FORMS OF THE INVENTION

There are two other transgene induction methods in current use. One relies on compounds in the tetracycline class of antibiotics, the other depends on the antiprogestin mifepristone (commonly known as RU486). Potentially the caging approach could be applied to yield caged tetracyclines and caged antiprogestins for use in those inducible gene expression systems, and thus extend their power and utility.

NOVEL FEATURES

No comparable method for rapidly and spatio-selectively activating gene expression.

APPLICATIONS OF THE TECHNOLOGY

1) Research in developmental biology.
2) Any application where rapid and selective activation of an exogenous gene is critical.
3) As a model for extending gene therapy applications.

Research Plan a. Specific Aims

The overall aim of this project is to develop a "light switch" methodology for rapidly triggering gene expression with high spatial and temporal resolution through the use of light. The project has three Specific Aims:

1) Chemical synthesis of a bio-inactive photosensitive reagent that, when illuminated with light, rapidly transforms into an inducer of gene expression.
2) Construction of a cell line stably expressing the necessary protein machinery that, when activated by the photo-generated inducer, will activate expression of a reporter gene.
3) Using the stable cell line to validate the "light switch" induction methodology.

b. Background and Significance

Inducible Gene Expression

Precise control of gene expression is useful in studying a wide spectrum of biological problems including development, cell cycle regulation and various physiological and neurobiological processes. In order to address such problems effectively, methods for controlling gene expression should ideally allow rapid, robust and reversible induction of gene expression in a spatially-selective manner. Thus, target genes may be turned on at will in specific cells or cell types.

At present, four externally-controllable systems are used to varying degrees to induce transgene expression (a more detailed discussion is given in the first part of Research Design and Methods). These systems are inducible either by antibiotics of the tetracycline family (Gossen and Bujard 1992; Gossen et al. 1995), by the progesterone antagonist, mifepristone (RU486) (Wang et al. 1994, 1999), by analogues of the insect molting hormone, ecdysone (No et al. 1996), or by synthetic ligands based on immunosuppressants such as FK506 that normally bind to endogenous immunophilins (e.g. FK506-binding proteins or FKBPs) (Clackson et al. 1998; Pollock and Rivera 1999). All four systems share two common features: 1) the method of induction is designed to turn on a target transgene of interest, but not endogenous genes, and 2) the inducer is a small organic molecule.

Temporal and Spatial Control of Gene Expression

A shortcoming of current methodology is a lack of real temporal and spatial control. In the temporal domain, activation of gene expression can be intrinsically very fast. It is known that hormone-induced interactions of nuclear receptors with coactivators can occur within 1–2 minutes (Llopis et al. 2000). Histone hyperacetylation (Chen et al. 1999) and chromatin restructuring occur within 10 minutes of hormone stimulation (Zaret and Yamamoto 1984; Archer et al. 1994). Recruitment of estrogen receptors to estrogen-responsive promoters occurs within 15 minutes, as does association of RNA polymerase II (Shang et al. 2000). Transcription is detected on a similar time scale (e.g., Ucker and Yamamoto 1984). Indeed, relevant to the ecdysone-inducible system, activation of gene expression in Drosophila by the steroid molting hormone through its nuclear receptor is equally rapid, with corresponding appearance of puffing on polytene chromosomes in under 5 minutes (Ashburner et al. 1974). These observations suggest that gene expression under control of nuclear receptors can occur extremely rapidly. An important advantage of an inducible expression system lies in the potential ability to turn genes on and off quickly, thus allowing manipulation of physiology at the cellular level with high temporal resolution. In all four regulable expression systems above, induction occurs by addition of the inducer molecule to the biological preparation. Therefore, pharmacokinetics, rather than the intrinsic kinetics of transcriptional activation, define the timescale on which gene activation may be induced. That is, the speed with which the inducer enters tissue and penetrates into cells becomes rate limiting in gene activation. Likewise, washout of inducer molecules limits the rate at which induction may be terminated. Applying inducer by conventional means thus degrades the high temporal resolution that is potentially achievable with an inducible expression system. Precise temporal control of induction and the ability to achieve pulsatile induction are expected to be most useful in situations where events unfold on a compressed timescale and where appearance of an important gene product is normally transitory—e.g., in studies of cell cycle regulation, development, or metamorphosis.

In the spatial domain, by placing expression of the induction machinery under tissue-specific promoter control, expression of a target gene may be induced in a particular tissue (see Pittius et al. 1988, and Robinson et al. 1995, for use of mammary tissue-specific promoter; see Tsien et al. 1996, for targeting to brain subregions). Tissues, however, are structurally complex networks of cells that are almost always functionally coupled. Current methods do not allow a target gene to be activated only in a subset of cells from a functionally distinct cell population within a tissue (e.g., expressing a potassium channel to suppress excitability in only selected pyramidal neurons in the hippocampus). Therefore, the advantage that comes from the ability to modulate the function of part of a tissue with high spatial resolution, while the rest of the same tissue remains "normal" or serves as control, is not realized. Precise spatial control of induction is expected to be most useful where it is important to observe the effects of a subpopulation of altered cells on a network of functionally and/or physically coupled cells (e.g. neural circuits in structures such as the visual cortex), or where a specific gene product with a defined spatial distribution has a morphogenetic role (e.g. in development).

Achieving Spatial and Temporal Control of Gene Expression through a "Caged" Inducer This proposal is aimed at developing a methodology for using focused light flashes to activate gene expression without delays associated with slow drug access to the induction machinery. Moreover, because light beams can be easily focused and directed at specific target locations, photoactivation is intrinsically spatially selective. At the core of the proposed methodology is a "caged" inducer molecule[1]—a photosensitive but biologically inactive precursor molecule that that can be loaded into, and accumulated in, cells and tissues. Upon exposure to light at the appropriate wavelength, the precursor is transformed photochemically into the active inducer molecule almost instantaneously (typically$\leq 1$ ms). Because the inducer is generated intra-cellularly in situ, interaction with the induction machinery occurs immediately to activate transcription. Therefore, "photo-release" of the inducer molecule greatly enhances spatial and temporal control over induction of gene expression.

[1]Photosensitive caged molecules were first introduced into biological research in 1978 (Kaplan et al. 1978). Real growth in the field began in the late 1980s, with the emergence of caged inositol-1,4,5-trisphosphate (Walker et al. 1987), followed by caged $Ca^{2+}$ (Adams et al. 1988; Ellis-Davies and Kaplan 1988), caged "anti-calcium" (Adams et al. 1989), other caged second messengers (diacylglycerol, Harootunian et al. 1991; cyclic ADP-ribose, Aarhus et al. 1995; cyclic nucleotides, Hagen et al. 1996), caged hormones (Muralidharan et al. 1993), caged neurotransmitters (Milburn et al. 1989; Wieboldt et al. 1994a,b; Rossi et al. 1997; Gee et al. 1999), caged gaseous messengers (NO, Makings and Tsien 1994; CO, Kao and Keitz 1997), caged enzyme cofactors (Salerno et al. 2000), caged $Ca^{2+}$-ATPase inhibitor (Rossi and Kao 1997), and caged proteins (Ottl et al. 1998). These reagents have been used in numerous studies where rapid in situ photo-generation of bioactivity (e.g. muscle contraction, DelPrincipe et al. 1999; Cifuentes et al. 2000) and/or spatial control of bioactivity (e.g. using caged neurotransmitter photostimulation to map brain circuitry, Roerig and Kao 1999) was crucial.

The Photoreleased Inducer Should be a Hydrophobic Molecule

Once photoreleased, the hydrophobicity of the inducer molecule determines the temporal characteristics of gene activation. Because the inducer is released in situ, induction is rapid. The effect of the inducer is then progressively attenuated as the photoreleased molecules are cleared from the cell. Cellular membranes are much more permeable to hydrophobic molecules than to hydrophilic ones. Consequently, the intracellular residence time of hydrophobic inducers is expected to be shorter than that of hydrophilic inducers. Therefore, in order to achieve rapid on-off switching, it is preferable that the inducer be hydrophobic.

Diffusional Dilution of Photoreleased Inducers Determines Spatial Resolution

When inducers are photoreleased at the focal point of the photolysis light beam, they will spread by diffusion in three dimensions. The volume enclosed by a sphere centered at the focal point increases as the third power of the radius. Therefore, as inducers diffuse away from the site of photorelease, their concentration drops off very sharply with increasing distance from the site of release. Spatially, the inducer concentration is always highest at the site of release and, after termination of the light flash, it decreases with time as diffusion dissipates the photo-released molecules. Given that it is preferable to have a hydrophobic inducer that can diffuse away so that gene induction could be readily terminated, the simple arguments presented here suggest that diffusion will always ensure that cells distant from the site of release never see high levels of inducer. Finally, it should be noted that the duration over which inducer levels remain elevated is under experimental control-varying the duration and frequency of light flashes results in different temporal profiles of inducer release.

The foregoing discussion suggests that a caged inducer of gene expression is feasible and can potentially enable a high degree of spatial and temporal control over the induction of gene expression.

c. Preliminary Studies

Synthesis of a Non-Steroidal Ecdysoid (NSE)

Through a sequence of eight chemical steps, we have synthesized a NSE of the bisacylhydrazine family, namely, 1-(3,5-dimethylbenzoyl)-1-tert-butyl-2-(2-ethyl-3-methoxybenzoyl)hydrazine (hereafter referred to as NSE-1). All synthetic reactions used were based on published reports (Meyers et al. 1974; Meyers and Mihelich 1975; Oikawa et al. 1994a,b; Shimizu et al. 1997). The chemical synthesis is shown in Scheme 1.

Scheme 1
Chemical Synthesis of a Non-Steroidal Ecdysoid (NSE)

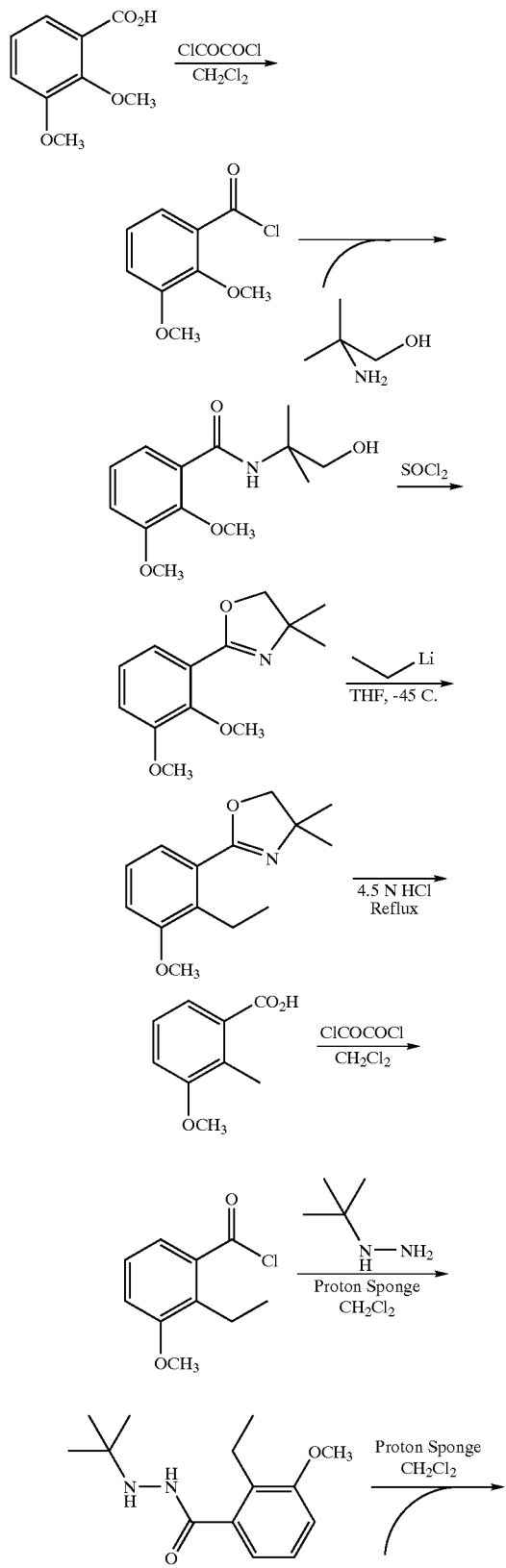

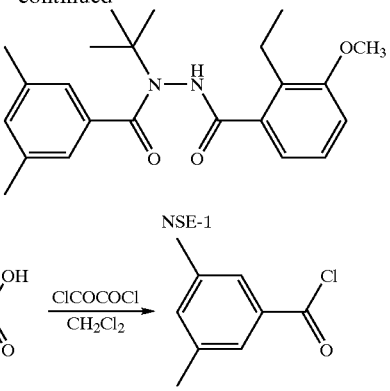

All molecules were purified by column chromatography and/or recrystallization. All structures were confirmed by $^1$H-NMR and by high-resolution fast atom bombardment mass spectrometry (FABMS).

Assessing NSE Toxicity In vitro and In vivo

Toxicity of NSE-1 in Cell Culture

Cellular toxicity of NSE-1 was tested in cell culture. NIH3T3-ER fibroblasts (Stratagene) were seeded into 96-well plates, allowed to attach for 24 hours in DMEM supplemented with 10% v/v fetal bovine serum (FBS). The medium was then replaced with DMEM-10% FBS containing ecdysoid drugs or solvent vehicle. Ethanol and DMSO were vehicle controls for ponasterone A and NSE-1, respectively. The cells were allowed to grow for 48 hours, at the end of which the cells were permeabilized and the amount of DNA in each well quantified with the CyQuant assay (Molecular Probes). Neither Ponasterone A at 10 $\mu$M, nor NSE-1 at 10, 30 or 100 $\mu$M significantly affected the growth capacity of the cells. The data are summarized in FIG. 1 (each measurement is the mean of 6 wells). These data indicate that NSE-1 is not cytotoxic and, therefore, can serve as the chemical basis of a photo-inducible gene expression system.

Toxicity of NSE-1 in Animals

NSE-1 was suspended (32.5 mg/ml) in vehicle consisting of 15% w/v Pluronic F127 surfactant (BASF Corp., Wyandotte, Mich.) and 3% v/v dimethylsulfoxide in phosphate buffered saline (PBS, pH 7). Intraperitoneal injections of this formulation (six 200-$\mu$l aliquots administered at 12-hour intervals) into 8 mice did not produce any signs of intoxication. These preliminary results suggest that NSE-1 is, at the very least, not acutely toxic to mammals, and thus should be usable in vivo in transgenic animals.

Placing EGFP Reporter Gene under Ecydysone Promoter Control in pEGSH Plasmid

Constructing the pEGSH-EGFP Plasmid

Figure 3:
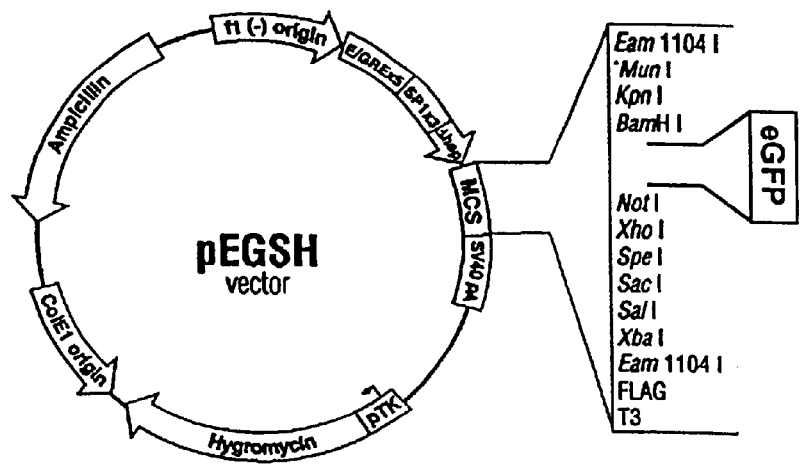
Figure 4:
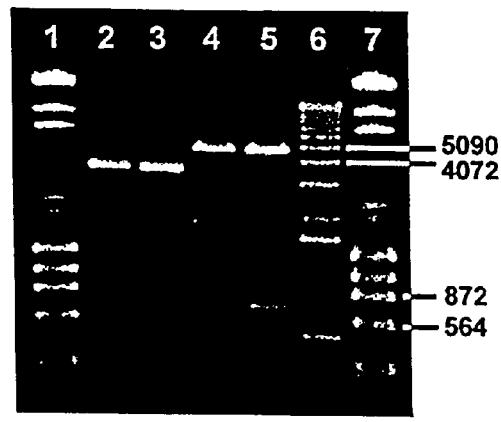

The pEGSH vector from Stratagene carries an ecdysone-inducible expression cassette, which includes five copies of a modified ecdysone-response element (No et al. 1996), and a multiple cloning site into which a target gene of interest may be inserted (FIG. 3). The vector also contains a hygromycin-resistance gene, so that mammalian cell transfectants can be selected with the antibiotic hygromycin. Using BamH1 and Not1 restriction, we excised the "enhanced green fluorescent protein" (EGFP) gene from the Clonetech pEGFP-1 vector, and inserted it into the multiple cloning site of the pEGSH vector. Restriction of the amplified and purified plasmid with BamH1 and Not1 gave the anticipated fragments (FIG. 4; lanes 1, 6 and 7 are size standards, with relevant size markers labeled, lanes 2 and 4 are the unrestricted circular plasmids, lanes 4 and 5 are fragments from restriction digest with BamH1 and Not1; expected fragment sizes are 4814 bp and 741 bp). That the EGFP gene was inserted in the proper orientation in the plasmid was verified by sequencing.

Induction of Reporter Gene Expression in Transiently-Transfected Cells

NIH3T3-ER cells, in which expression of a modified ecdysone receptor and the retinoid X co-receptor are driven by the CMV promoter, were transiently transfected with the pEGSH-EGFP plasmid using FuGene 6 transfection reagent. The transfected cells were treated with 30 µM NSE-1 or vehicle for 48 hours and then screened for induction of EGFP expression by single-cell microfluorimetry. The results are shown in FIG. 2. These results demonstrate the efficacy of NSE-1 in inducing transgenes in cultured cell lines.

The above experiments show that the pEGSH-EGFP plasmid was properly constructed and that NSE-1 can induce EGFP reporter expression when the plasmid was transfected into the proper background. These results suggest that the pEGSH-EGFP plasmid could be used for making stable, inducible cell lines from NIH3T3-ER cells.

NSE-1 Induction of Reporter Genes in Primary Rat Anterior Pituitary Cells after Adenovirus-Mediated Gene Transfer Anterior pituitary glands were removed from female Sprague-Dawley rats, enzymatically dissociated, and plated onto No. 1 polylysine-coated glass coverslips for culturing as previously described (Ho et al. 1995). The cells were doubly infected with one adenovirus (AdVgRXR) that allows constitutive expression of a modified ecdysone receptor (VgEcR) and the retinoid X receptor (RXR) and a second adenovirus (AdGFIRK) that places under ecdysone promoter control the expression of a fusion protein between EGFP and a potassium channel of the inward rectifier family (Kir2.1). For infection, the adenoviruses were applied at 200 pfu's per cell in infection medium for 3–5 hours. The cells were then allowed to recover for 24 hours before being treated with ecdysoids (ponasterone A, NSE-1) or solvent vehicle for 24 hours.

Figure 5:
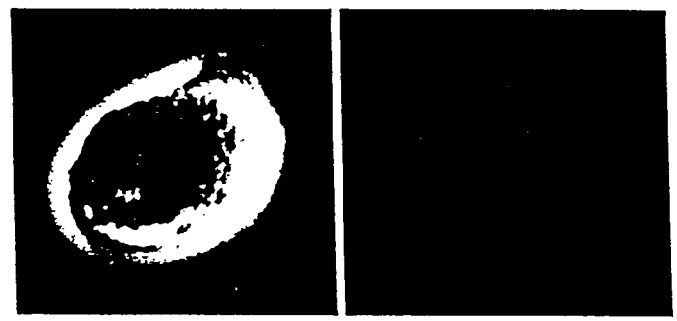
Figure 6:
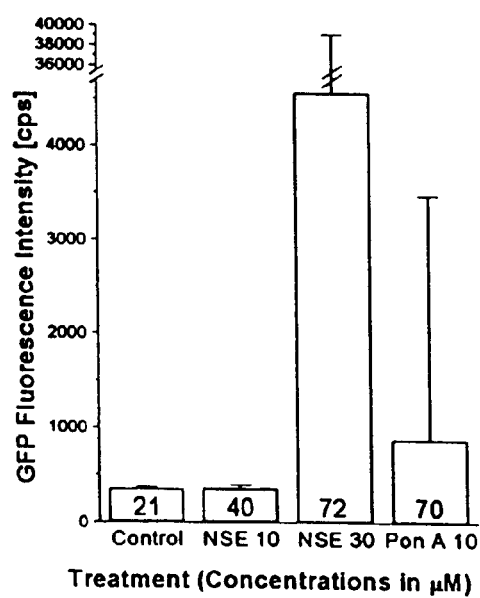

After induction, cells were then randomly chosen through a phase-contrast view and EGFP expression in each chosen cell was monitored by single-cell microfluorimetry. Phase-contrast and fluorescence microscopic images of an induced cell are shown in FIG. 5. Because the EGFP-Kir2.1 fusion protein should be targeted to the plasma membrane, we expect its presence in the plasma membrane as well as in the Golgi-as the images in FIG. 5 indeed illustrate. A quantitative summary of the microfluorimetric data is shown in FIG. 6 (note break in y-axis scale; N shown at the base of each bar). The results show that NSE-1 and ponasterone A both can strongly induce expression of the EGFP-Kir2.1 fusion protein. In FIG. 6, the "standard errors" shown by the error bars do no indicate lack of reproducibility in the measurement technique, but rather give a sense of the wide variations of expression levels within the induced cell population. These results demonstrate more quantitatively the utility of NSE-1 as an inducer of the ecdysone-dependent expression system.

(The experiments involving adenoviruses were performed in collaboration with Dr. Karen Gregerson, Dept. of Physiology, Univ. of Maryland School of Medicine.)

d. Research Design and Methods

There are three important steps in developing a photoinducible gene expression system that must be considered:

1) selecting an existing gene expression system that is inducible by a small molecule upon which the design of the "caged" inducer may be based, 2) designing routes of chemical synthesis that would yield caged inducers with desired properties, and 3) constructing a biological test system in which the workings of the photoinducer could be validated.

These issues will be discussed below.

Selecting the Basic Inducible Gene Expression System

Over the last decade, a number of inducible gene expression systems have been developed and have been utilized to varying extents. These include systems inducible by antibiotics of the tetracycline family (Gossen and Bujard 1992; Gossen et al. 1995), by the progesterone antagonist, mifepristone (RU486) (Wang et al. 1994, 1999), by analogues of the insect molting hormone, ecdysone (No et al. 1996), and by synthetic ligands based on immunosuppressants such as FK506 that normally bind to endogenous immunophilins (e.g. FK506-binding proteins or FKBPs) (Clackson et al. 1998; Pollock and Rivera 1999). In each case, the inducer is a small molecule amenable to structural manipulations through synthetic organic chemistry. Choosing one of the above systems as the starting point for developing a photoinducible gene-switch requires evaluation of the relative merits of the existing systems, and deciding which practical compromises, if any, one should accept.

Synthetic Dimerizers Based on FK506 and FKBP

The system based on synthetic FK506-like ligands and recombinant FKBPs is an exciting innovation in externally regulable gene expression. It is, however, still quite early in development and not easily accessible. Moreover, vectors for introducing the inducible expression machinery into living cells and tissues are only just being developed (Pollock et al. 2000). Therefore, the "synthetic-dimerizer" system is not, at present, a good basis for a photoinducible gene-switch.

The RU486 System

At the core of the RU486 system is the human progesterone receptor with a C-terminal 42-aa deletion. This truncated receptor shows no affinity for progesterone but still exhibits high affinity binding to mifepristone (RU486), a synthetic antiprogestin, to activate gene expression. A chimeric transactivator was created by fusing the ligand binding domain of the mutant progesterone receptor to the GAL4 transcriptional activator from yeast, which contains DNA-binding, dimerization and nuclear localization domains, and to the activation domain of VP16 protein from herpes simplex virus (HSV) (Wang et al. 1994). Replacing the DNA-binding domain of the progesterone receptor with that of GAL4 ensured that the transactivator will not activate any endogenous progesterone-responsive genes. Furthermore, because mammalian DNA is not expected to have GAL4 binding sites, the engineered transactivator is not expected to turn on other endogenous genes either. When bound to RU486, the transactivator binds to GAL4-binding elements located 5' to a thymidine kinase promoter, which drives expression of the target or reporter gene. Although some background expression in the absence of RU486 was seen in the original experiments (Wang et al. 1994), later studies did show tight regulation of expression (Tsai et al. 1998). The antiprogestin inducer, mifepristone/RU486, is a synthetic steroid that is highly effective in activating the chimeric transactivator. In vitro, RU486 induces transcription of transgenes at concentrations of only a few nanomolar. In transgenic mice, a single intra-periton-eal injection of mifepristone suspension in oil at 250 µg/kg body weight (equivalent to at most a few tens nanomolar averaged over whole body) elevated transgene expression by 1500-fold (Wang et al. 1999). Adenoviral vectors for transferring this regulable expression system have also been developed (Molin et al. 1998; Burcin et al. 1999).

Figure 7:
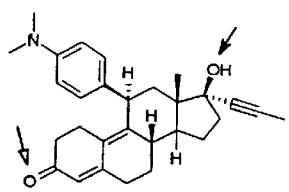

There are three practical reasons why the RU486 system may not be ideal as the basis for a photoinducible expression system. First, the very high sensitivity of the system to induction by mifepristone is biologically advantageous, but may be potentially problematic in a situation where light is used for photochemical activation. Delivering an accurately-controlled and small dose of light focally to generate a very low concentration of an inducer molecule in a restricted volume in a multicellular preparation is likely to be difficult. Because such low concentrations of RU486 are required, over-photolysis and light scattering would be expected to degrade the spatial resolution of the photo-switching technique. Second, mifepristone is a steroid (see FIG. 7) with two functional groups that are potential targets for caging: a hydroxyl (marked by solid arrow in FIG. 7) and a conjugated carbonyl (open arrow). We have developed cages that would be suitable for each of these functional group (the Nmoc cage for the hydroxyl: Rossi and Kao 1997; the 2'-nitro-2, 3-dihydroxy-dihydrocinnamates for the carbonyl: Kao and Keitz 1997), and thus might be expected to be useful in direct reaction to generate a caged mifepristone. Our somewhat limited experience with bioactive steroids, however, is that they are prone to side reactions, and chemical manipulations often require extensive use of protective groups to block such unwanted reactions. As a starting point for testing the concept of a photochemical gene switch, steroid-based inducers may prove intractable. Finally, because mifepristone antagonizes the action of the steroid hormone progesterone, its suitability as an inducer of expression in a wide spectrum of model systems may be questionable. For example, in models of mammary gland development, it is potentially inform-ative to turn on genes that regulate apoptosis (e.g. the Bcl-2 gene family) in a spatially and temporally controlled manner. Progesterone at nanomolar levels stimulates growth of mammary alveolar epithelia. In such a case, using an expression system where the inducer is an antiprogestin is potentially confounding (despite the disclaimer that antiprogestin concentrations used to terminate early pregnancy is typically at least two to three orders of magnitude higher than those used for induction of gene expression). Thus, in any study where female reproductive endocrinology is important, use of antiprogestins like mifepristone could have potentially undesirable (or worse, unanticipated but unseen) effects. Because of the above three considerations, we decided not to use the RU486 system as the basis for a photoinducible switch.

The Tetracycline-Regulable System

Repressible system. The tetracycline-regulable system began as a repressible system (Gossen and Bujard 1992), the basis of which is the repressor protein that negatively regulates expression of tetracycline (Tc) resistance in *E. coli*. In the absence of Tc, the repressor binds to the Tet operator and suppresses expression of the Tc-resistance gene. In the regulable system, a strong promoter drives expression of a synthetic transactivator protein ($tTA_R$), which is a fusion of the Tet repressor with the C-terminal activation domain of VP16 protein of HSV. The VP16 domain is a strong activator of mammalian promoters. In the absence of Tc, $tTA_R$ binds to Tet operator sequences and activates a downstream promoter which drives the expression of a target or reporter gene. When Tc is present, it forms a high-affinity complex with $tTA_R$ which has greatly-reduced affinity for the Tet operator sequences. Tc thus suppresses expression of the target gene.

Inducible System. A mutation in $tTA_R$ converts it from a Tc-repressible to a Tc-inducible transactivator ($tTA_I$) (Gossen et al. 1995). In the absence of Tc, $tTA_I$ has little affinity for Tet operator sequences. When in complex with Tc, however, $tTA_I$ binds to the Tet operator sequences and activates the downstream promoter to drive expression of the target or reporter. In contrast to the repressible system, here, Tc activates target gene expression. One advantage of the Tc-inducible system over the repressible system is that tetracyclines need not be chronically administered, because tetracyclines have cytotoxic effects (Gossen et al. 1995). In addition to tetracycline cytotoxicity, another potential issue is the cytotoxicity of overexpressed $tTA_{R/I}$ proteins, which has been reported in several systems (Gossen et al. 1992; Baron et al. 1997; Yrjanheikki et al. 1998).

The Tc-inducible system has shown some evidence of background expression in the absence of Tc (No et al. 1996), or "leakiness". In transgenic animals where the system has been used, however, any leakiness, if present, appeared to have had no confounding effects. Part of the explanation for why leakiness might be of less concern in animals may lie in compensatory mechanisms that whole organisms could enlist to suppress the effects of low levels of transgene products and maintain homeostasis.

Figure 8:
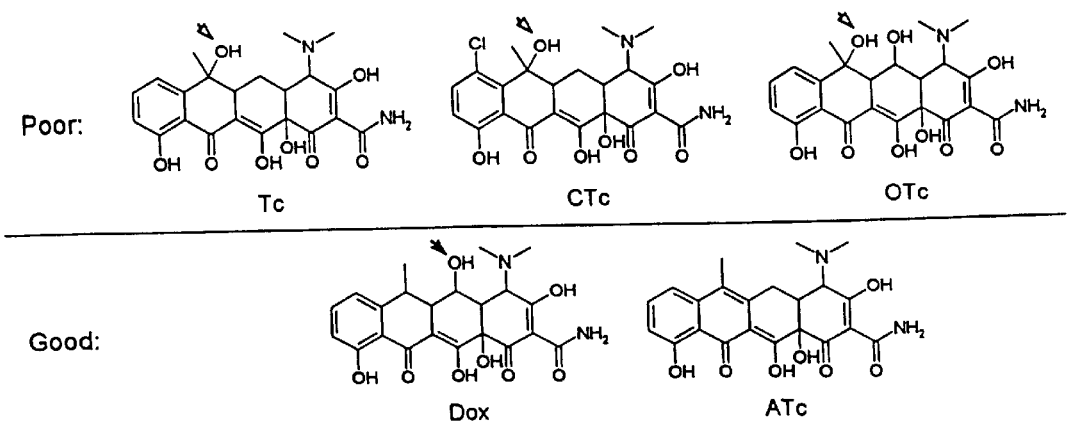

All members of the tetracycline family of antibiotics are not equally effective in the Tc-based systems (Gossen et al. 1995). Of those tested, doxycycline appears to be the most potent inducer. Structures of good and poor inducers in the Tet system are shown in FIG. 8 (CTc is chlortetracycline; OTc, oxytetracycline; Dox, doxycycline; ATc, anhydrotetracycline). Structural comparison reveals that a hydroxyl group at position 6 (open arrows) is detrimental to inducing activity, and also suggests that structural features on the "northern" side of the 4-ring tetracycline nucleus might be more important in binding. Given that doxycycline only has a single hydroxyl group at the 5-position (filled arrow) on the northern face of the molecule, that hydroxyl appears to be the best functional group to which to attach a photosensitive cage to ensure abolishing inducing activity in the absence of photolysis. The chemical complexity of the problem lies in the existence of several other hydroxyl groups around the molecular frame-caging the 5-hydroxyl specifically would not be an easy task. All other potential reactive functional groups must be masked before position 5 can be safely manipulated. This difficulty, although not insurmountable, makes direct modification of doxycycline chemically unattractive.

Finally, the tetracyclines, by virtue of having multiple hydrophilic functional groups, are quite soluble in water. While high aqueous solubility makes drug administration easier, it makes penetration into, and clearance out of, cells slow. This lack of fast diffusive dissipation would severely degrade the potentially excellent temporal control made possible by photorelease.

The Ecdysone-Regulated System

The ecydysone-regulable gene expression system relies on a recombinant ecdysone receptor (VgEcR), which is an N-terminal truncation of the natural ecdysone receptor from D. melanogaster fused to the activation domain of VP16 from HSV; VgEcR also bears 3 point mutations in the P box of the DNA-binding domain of EcR to resemble that of the glucocorticoid receptor (GR) to allow recognition of a synthetic ecdysone-response element (E/GRE), which consists of inverted half-site recognition elements for the retinoid X receptor (RXR) and GR DNA-binding domains. The hybrid E/GRE sequence is designed to evade recognition by any endogenous nuclear receptors. With RXR, the vertebrate homologue of Drosophila ultraspiracle (Yao et al. 1992), VgEcR forms a heterodimer that binds to E/GRE and initiates transcription. The ecdysone-inducible expression system has very low basal expression (No et al. 1996), because the presence of ecdysoid hormones is obligatory for receptor heterodimerization and DNA binding (Yao et al. 1993). Finally, ecdysoid hormones have no known corresponding bioactivity in vertebrates, presumably because there are no processes homologous to molting.

Figure 9:
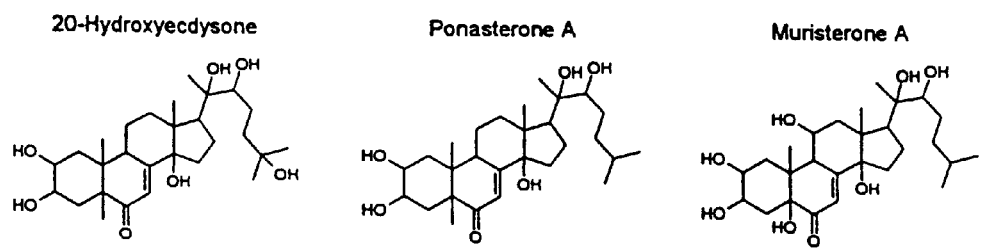

The ecdysone receptor is moderately activated by the natural molting hormone, 20-hydroxy-ecdysone, and much more robustly activated by two ecdysteroids of plant origin, ponasterone A and muristerone A (see FIG. 9). That these ecdysone analogues are steroids presents the same chemical obstacle to caging as did mifepristone. Fortunately, however, members of the bisacylhydrazine family are potent activators of the ecdysone receptor, and they are accessible by facile organic synthetic routes. As shown in Preliminary Studies, we have successfully synthesized a non-steroidal ecdysoid (NSE) from this class of compounds. Our NSE-1 proved to be as active as ponasterone A in inducing expression of reporter genes under ecdysone promoter control. The concentrations of NSE-1 required for activating the ecdysone system is comparable to that of ponasterone A—in the $\mu$M range—concentrations easily and reliably generated in situ by photolysis (Rossi and Kao 1997). Furthermore, because non-steroidal mimics of ecdysoid molting hormone have been of great interest to the agrichemical business, the acute toxicity, mutagenicity, carcinogenicity, and teratogenicity of the bisacylhydrazine family of NSEs have been extensively tested since the compounds were serendipitously discovered as ecdysone mimetics in 1983 (see Dhadialla et al. 1998 and references therein).

Introduction of adenoviral vectors to mediate gene transfer greatly enhanced the utility of the ecdysone-inducible system. To date, studies of the effects of ecdysone-induced gene expression after adenovirally-mediated gene transfer have been successfully performed in vitro and in vivo (Johns et al. 1999; Holt et al. 1999; Hoppe et al. 2000a; Perez-Garcia et al. 2000).

Finally, despite its many advantages, there is one potential drawback to the current implementation of the ecydysone-inducible system-the inducer is a heterodimer of RXR with Drosophila EcR, both of whose exogenous genes must be constitutively expressed at high levels in cells where ecdysone-inducible expression of a target gene is desired. This makes the ecdysone system more complex than the tetracycline or RU486 systems. Because RXR is normally present in mammalian cells, the need for over-expression of RXR as a condition for EcR function seems puzzling. The answer, already known for some time, is that mammalian RXR is a relatively poor substitute for its homologue, ultraspiracle, in heterodimerization with Drosophila EcR (Thomas et al. 1993; Yao et al. 1993). Comparative studies revealed that EcR from the silkworm, *Bombyx mori*, was strongly activated by ecdysone agonists even in the absence of exogenous RXR (Suhr et al. 1998). Differences in the hormone-binding and "hinge" domains of EcRs from Drosophila and Bombyx appear to account for the difference in affinity for RXR and therefore the ability to heterodimerize with RXR at endogenous levels (Suhr et al. 1998). This knowledge has now been used to engineer a chimeric Drosophila-Bombyx ecdys-one receptor (DB-EcR) whose function no longer requires exogenous RXR supplementation. This approach has been validated through adenovirus-mediated gene transfers in vitro and in vivo (Hoppe et al. 2000b). The innovation represented by DB-ECR minimizes the complexity of, and thus should enhance the power and utility of, the ecdysone-inducible system.

Because the ecdysone system appears to be non-leaky, is not cytotoxic, is transferable by viral vectors, is induced robustly by small biocompatible molecules that are readily accessible through organic synthetic chemistry and at concentrations easily achievable by photolysis, and is under continued active improvement, we decided to use the ecdysone-inducible system as the basis for developing a photo-inducible gene switch.

Caging of NSE-1 to Yield a Photo-Releasable Ecdysone Analogue

Figure 10:
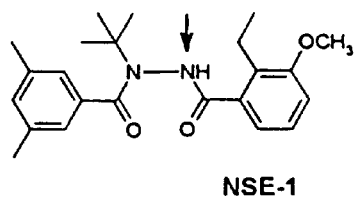

Examining the structure of NSE-1 (FIG. 10) shows that there is only one position in the molecule that is still open for chemical modification, namely the $N^2$ position (marked by arrow in FIG. 10). Any caging group must therefore be covalently linked to the $N^2$ position. Precisely how the linking reaction is to be performed will be presented after discussing the functional criteria that a caged NSE must meet, as well as the molecular design of the caging group.

Functional Criteria for a Caged NSE

Ideally, a practical photoreleasable, or caged, NSE should meet the following criteria:

1) before photolysis, it must be inactive in inducing the ecdysone-regulable expression system,
2) it must be photolyzable with long-wavelength ultraviolet light (UV, 300–400 nm), or multi-photon equiv-alent, with reasonably high quantum yield, and
3) it can be accumulated or stockpiled in cells in highly water-soluble form by passive incubation with a precursor of the water-soluble form.

Criterion (1) is self-explanatory and will not be further discussed. Criterion (2) results from two practical considerations: avoidance of high-energy UV (<300 nm), which can damage proteins ($\lambda_{max} \approx 280$ nm) and nucleic acids ($\lambda_{max} \approx 260$ nm), and safeguarding against unintended photolysis by visible light. Moreover, a photolysis energy requirement in the 300–400 nm range makes the photolytic uncaging reaction accessible to current two-photon photolysis instrumentation (more below). Meeting criterion (3) means that by incubation with a precursor form, a cell can accumulate caged NSE intracellularly in a stockpile from which photolysis can generate active NSE.

Designing a Photolabile Cage to Meet the Functional Criteria

Most caging groups in current use are derived from a simple 2-nitrobenzyl group (see FIG. 11), which has an absorption maximum ($\lambda_{max} \approx 260$ nm), and a quantum yield (Q) for photo-release of>0.1 (Q=0.1 means 10% of absorbed photons actually lead to photo-release of desired product). Adding oxy-type substituents to the back end of the nitrobenzyl group pushes the absorption maximum into the long-wavelength UV region ($\lambda_{max} \approx 360$ nm; FIG. 11), with almost always a concomitant decrease in quantum yield, although Q does not drop below 0.1. Therefore, to satisfy criterion (2) above (long-wavelength UV absorption), the cage should incorporate oxy-substituents into a nitrobenzyl-type cage. (These and other aspects of the design and properties of caged molecules are extensively discussed in Kao and Adams, 1993).

Because NSE-1 itself is a hydrophobic molecule, the requirement that the caged NSE could exist in a very water-soluble form (first part of criterion (3) above) can only be met if the cage itself incorporates functional groups that confer high aqueous solubility. Since ionic groups have the greatest solubilizing power, they must be built into the cage. In the present case, carboxyl groups are most easily incorporated. The most straightforward way to combine the oxy-substituents for long-wavelength absorption and the carboxyl groups for solubility is in the form of the BcmNB cage (FIG. 12A).

Figure 13:
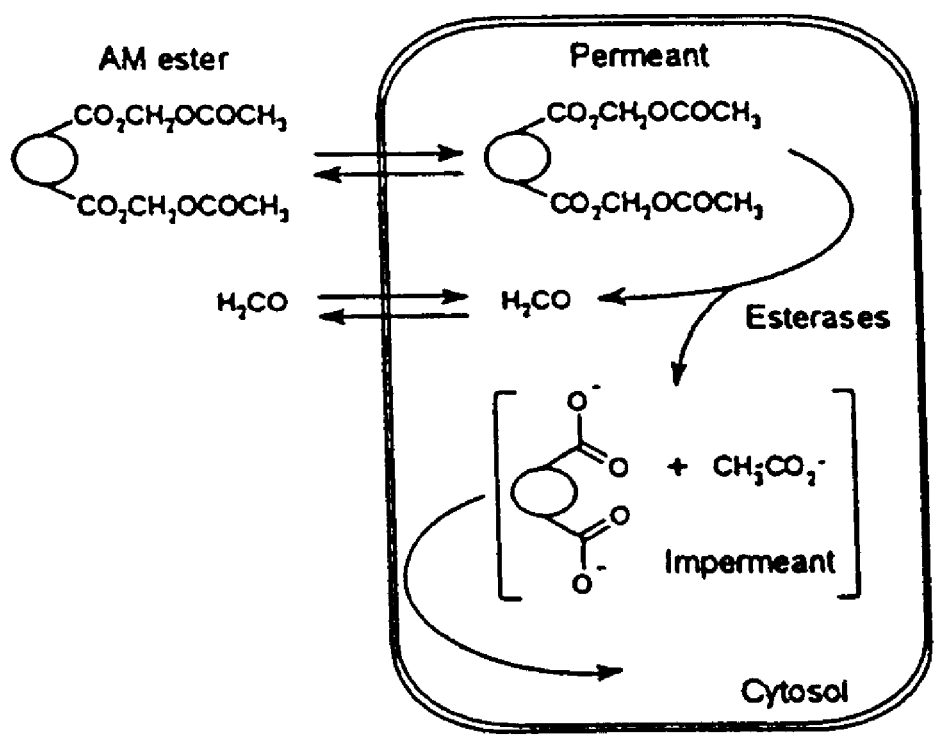

Meeting the second part of criterion (3)-having a precursor form of caged NSE-1 that could be passively loaded into cells by incubation and then accumulated intracellularly as a water-soluble form is most readily done by temporary masking of the carboxyls on the cage as acetoxymethyl (AM) esters (Tsien 1981; FIG. 12B), which are labile to hydrolysis by "nonspecific" intracellular esterases (FIG. 13). During incubation, AM esters, which are membrane-permeant, pass through the plasma membrane and enter the cell, where esterases rapidly cleave off the AM groups to liberate the free carboxylates. The carboxylates, being anions, are membrane-impermeant, and are thus trapped within the cell. Through this loading method, incubation with micromolar concentrations of AM ester in the extracellular medium allows millimolar concentrations of carboxylates to be accumulated inside cells. One important aspect of AM esters needs clarification. Hydrolysis of each AM ester liberates the target carboxylate, a free acetate, and one molecule of formaldehyde. While generation of formaldehyde seems alarming, the actual danger is negligible for at least two reasons: 1) formaldehyde is membrane-permeant and is readily lost by diffusion through cellular membranes as soon as it is generated; 2) formaldehyde is only generated in proportion to the concentration of extracellular AM ester available and therefore can never rise above the micromolar levels normally adopted in AM ester loading. It is for these reasons that in the nearly 20 years since AM esters came into cell biological and physiological use, there has been no evidence of damage from AM ester loading, either in cultured cells or in tissue preparations. Most importantly, acetoxymethyl and other acyloxymethyl esters have an even longer history as pro-drugs and continue to be a viable choice in the pharmaceutical field, which suggests that in intact organisms, AM esters do not pose any real risk (for recent examples, see Iley et al. 1997; Niemi et al. 2000).

Synthesis of the desired BcmNB cage, its use in caging NSE-1, and generating the AM ester form of caged NSE-1 will be described in subsequent sections.

Synthesis of BcmNB Caging Reagent

The proposed synthetic route for the BcmNB cage is shown in Scheme 2, below.

Scheme 2
Synthesis of Bcm-NB Caging Reagent

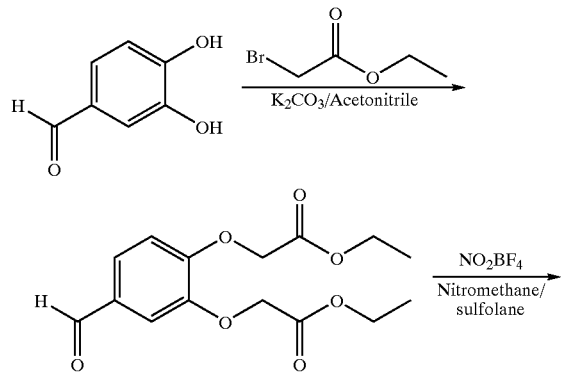

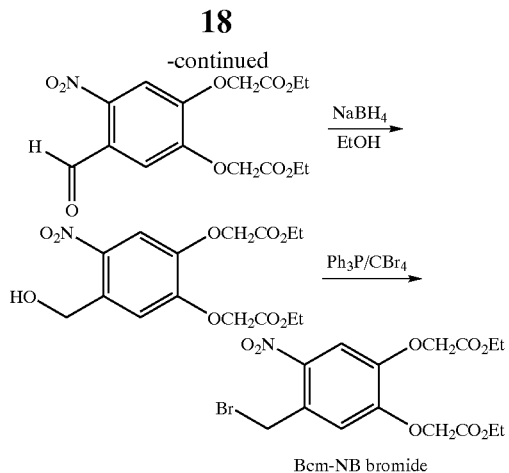

Bcm-NB bromide

In Scheme 2, all reactions are conventional except for the nitration reaction ($2^{nd}$ step). We decided to avoid using protocols requiring aqueous acid or acid mixtures for nitration, because of concern that strong acid/aqueous conditions would lead to hydrolysis of the two ethyl esters in the molecule. We propose using nitronium fluoborate ($NO_2BF_4$) for nitration in an anhydrous solvent mixture of sulfolane and nitromethane (Olah and Kuhn 1962; Olah et al. 1962). The nitronium ion is a highly reactive species that effects aromatic nitrations rapidly. The solvent mixture is dictated by reaction conditions. The reaction will be run at ~0° C. Sulfolane is a good solvent for nitronium fluoborate, but solidifies at room temperature. Nitromethane is an inert solvent with a freezing point of −29° C., but does not dissolve the nitrating reagent very well. By using nitromethane to lower the freezing point of sulfolane, we can run the reaction at 0° C. while maintaining the reaction mixture fluid. For the final step of Scheme 2, we choose to use the very mild combination of triphenylphosphine/tetrabromomethane to convert the benzylic alcohol into a benzylic bromide (Kang and Hong 1987; Lan et al. 1987).

Caging NSE-1 with BcmNB Caging Reagent

Two approaches to caging NSE-1 with BcmNB are possible. First, because benzyl bromides like BcmNB bromide are reactive, we could attempt direct reaction between NSE-1 and BcmNB bromide. Such a reaction would require using a strong base (e.g. sodium hydride) to deprotonate $N^2$ in NSE-1 and allowing the resulting anion to displace the bromide from BcmNB, as shown in Scheme 3.

Scheme 3
Direct Reaction of NSE-1 with Bcm-NB Bromide

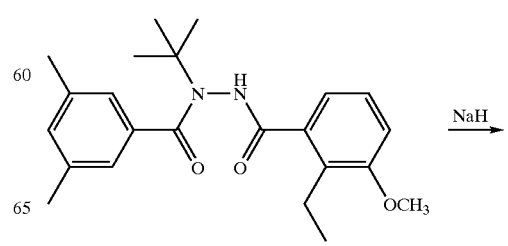

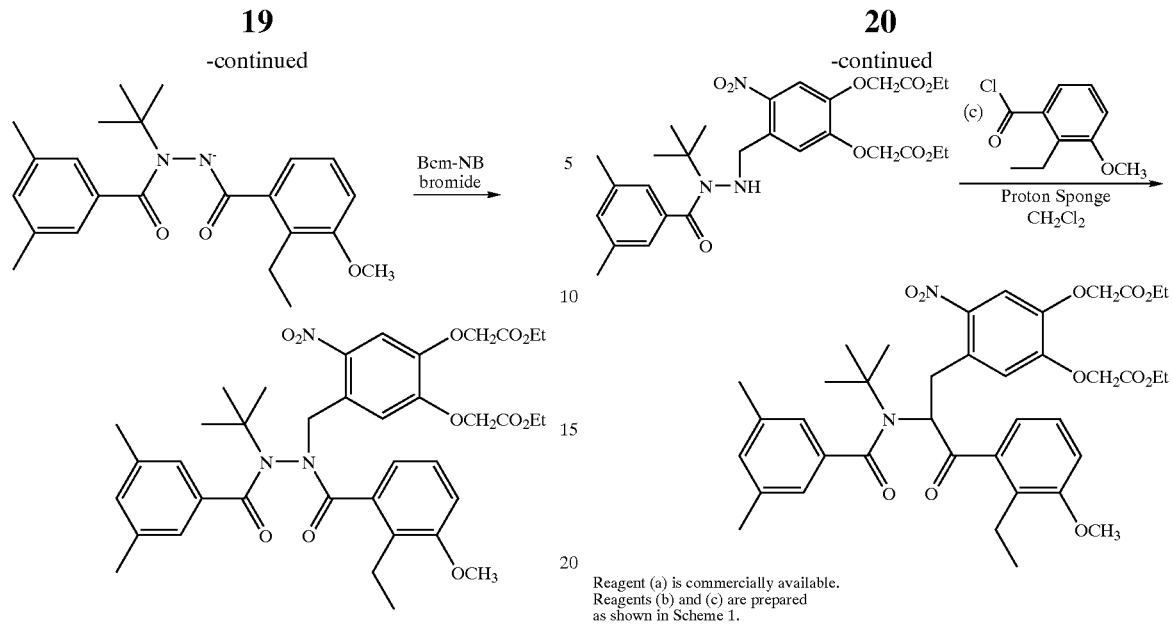

Reagent (a) is commercially available.
Reagents (b) and (c) are prepared as shown in Scheme 1.

While attractively short, this route is unlikely to be successful. In our experience, strong base conditions as those required to deprotonate the bisacylhydrazine are not compatible with caging groups like BcmNB. An alternative synthetic route is shown in Scheme 4.

Scheme 4 relies on the proven success of Scheme 1 for making NSE-1. Protecting the $N^2$ position with tert-butylchloroformate (reagent a) leaves the $N^1$ position open for acylation with acyl chloride b (prepared as in Scheme 1). Deprotecting with trifluoroacetic acid opens N2 to react with the caging reagent, BcmNB bromide. When thus alkylated, $N^2$ can still be acylated by acyl chloride c (again prepared as in Scheme 1) to yield the fully caged and protected NSE-1.

Preparation of the Free Salt and AM Ester Forms of BcmNB-Caged NSE-1

The sodium salt of BcmNB-caged NSE-1 is obtained by hydrolysis with sodium hydroxide in part-aqueous solution (Scheme 5, $1^{st}$ step). The AM ester form of caged NSE-1 is obtained by reacting the Na salt with commercially available bromomethyl acetate (reagent d, Scheme 5) following previously developed protocol (Rossi and Kao 1997).

Scheme 4
Synthesis of Bcm-Np Caged NSE-1

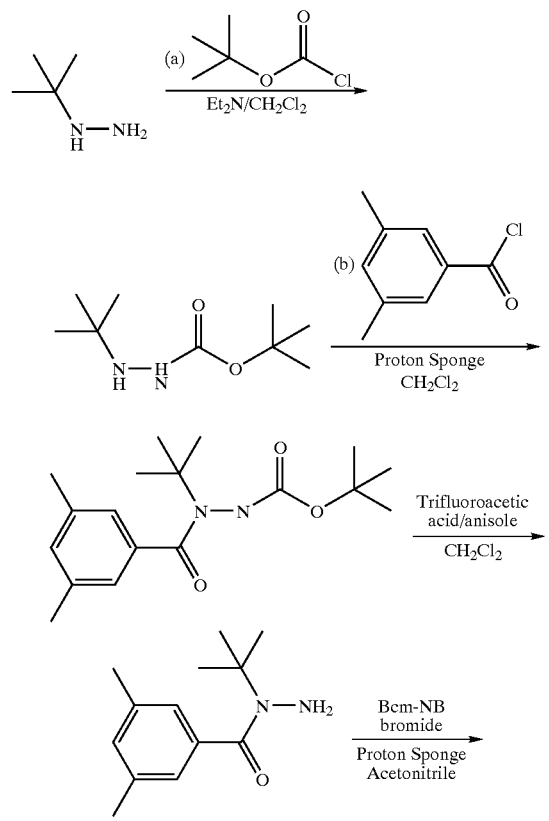

Scheme 5
Preparation of AM Ester Form of BcmNB-NSE-1

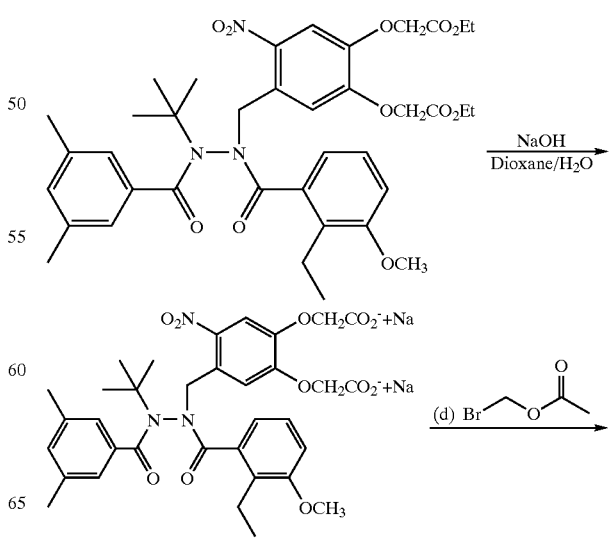

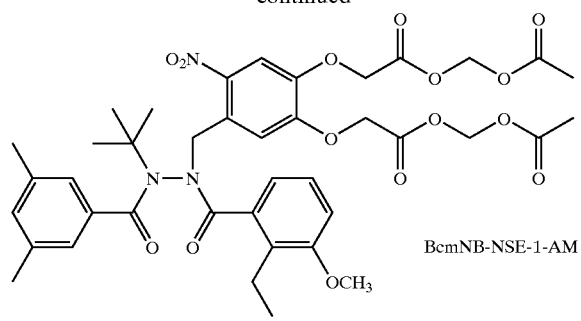

BcmNB-NSE-1-AM

Physico-Chemical Characterization of Caged NSE-1

The identity of all final products as well as all chemical intermediates will be confirmed by $^1$H-NMR and high-resolution fast-atom bombardment mass spectrometry (HR-FABMS). UV-visible absorbance spectra will be recorded on final products, thus allowing molar extinction coefficients to be determined for each key compound. Analytical chromatography as well as NMR spectroscopy will be used to ascertain that photolysis of caged NSE-1 liberates authentic NSE-1. Quantum yields of photolysis will be determined by established procedures (Rossi and Kao 1997; Rossi et al. 1997).

Test of AM Ester Loading into Cells; Quantitation of Intracellular Loading

Although AM ester loading is not expected to be problematic, it is nonetheless prudent to confirm that through incubation with NcmNB-NSE-1-AM, cells can cleave the AM ester and accumulate the dicarboxylate form of the caged NSE. We will assess BcmNB-NSE-1 loading into cultured cells essentially as previously described (Kao et al. 1989). NIH3T3-ER cells (to be used subsequently in biological testing of the caged NSE) will be cultured. Cell density will be determined by trypsinization and cell counting. Estimates of cell sizes will be made by measuring a suitable sample of cells under the optical microscope. Multiple plates of cultured NIH3T3-ER cells at equal density will be incubated with nominally 10–40 µM of the AM ester in aqueous medium (containing 0.02% w/v of the non-ionic surfactant Pluronic F127 to aid solubilization of the hydrophobic AM ester). At half-hour intervals, ~2 million cells will be washed free of the loading solution and permeabilized with 60 µM digitonin to release water-soluble cell contents. The lysate will be centrifuged to remove debris and clarified by centrifugal filtration through membranes of 0.2 µm porosity. The lysates will be lyophilized to reduce volume if necessary. The absorbance of the filtrates at the $\lambda_{max}$ of BcmNB-NSE-1 will be measured against lysates from unloaded cells in fused-silica spectrophotometric cells (3-mm diameter; 5-cm optical pathlength, 400-µl volume), although not much background absorption is expected near 360 nm. Using the extinction coefficient of the caged NSE, we can quantitate the BcmNB-NSE-1 in the lysate and infer the average whole-cell concentration in the intact cell population.

Given that the typical extinction coefficient for the dioxynitrobenzyl type cage is expected to be ~6000 $M^{-1}cm^{-1}$ at 360 nm, at an intracellular concentration of ~1 mM, $2\times10^6$ cells (typical cell volume ~2 µl per $10^6$ cells) will yield BcmNB-NSE-1 to give an absorbance of 0.3 in the 5-cm cylindrical cuvette. Because in a clarified cell lysate, absorbances of 0.05 can be reliably measured, this method of quantitation is expected to give good estimates of loading. Construction of Biological Test System to Validate BcmNB-NSE-1 as a Photochemical Gene Switch Once a caged NSE is in hand, its biological efficacy must be evaluated. We propose to test, in a stably transfected cell line, the ability of caged NSE-1 to turn on expression of a reporter gene under ecdysone promoter control.

Generating a Stable Doubly-Transfected Cell Line that Supports Ecdysone-Inducible Gene Expression CHO, HEK293 and NIH3T3 cell lines stably-transfected with pERV3 vector to allow constitutive expression of VgEcR and RXR are currently available (Stratagene). Of these three cell lines, we have already used the NIH3T3-ER line for transient transfection experiments (Preliminary Studies). We will use FuGene 6 reagent to transfect NIH3T3-ER with the pEGSH-EGFP plasmid described in Preliminary Studies. After 48 h, the transfected cells will be plated at low density in DMEM/10% FBS/1% SeaPlaque agarose under double selection: with G418 to maintain selective pressure for the pERV3 vector and hygromycin to select for PEGSH-EGFP. Emergent doubly antibiotic-resistant colonies will be lifted with the overlying soft agarose plaque, briefly trypsinized, and expanded in culture dishes under continued double selection. Each clone will be plated onto glass coverslips, treated with either ponasterone A or NSE-1, and screened for EGFP expression by fluorescence imaging. Clones with high levels of inducible EGFP expression will be retained (hereafter referred to as 3T3-ER/EGFP cells).

Testing BcmNB-NSE-1 as a Photoactivatable Gene Switch

Light Delivery for UV Photolysis. 3T3-ER/EGFP cells will be cultured on glass coverslips, mounted on an inverted fluorescence microscope (Eclipse TE200, Super Fluor 40X immersion objective, Nikon), and superfused with medium containing µM concentrations of BcmNB-NSE-1·AM to allow intracellular loading of the caged NSE. Cells will be photoactivated in two ways: wide-field illumination and focal illumination. In wide-field illumination, the output of an argon ion laser (Model 2065-7S, Spectra Physics, multiline UV emission$\geq$1 watt), attenuated as necessary, will be passed through a beam-expander and guided into the UV-transmitting fluorescence objective of the inverted microscope by reflection from a dichroic mirror. With the exception of the light source, the setup is as described in Rossi and Kao, 1997. Cells within the entire field of view in the microscope will be exposed to the UV light. Light flash duration ($\geq$1 ms) will be controlled by a laser shutter interposed between the laser head and the beam expander. In focal illumination, the UV output beam of the argon ion laser is launched into a quartz optical fiber (10–50 µm in core diameter). The output end of the fiber will be mounted on a micromanipulator on the inverted microscope to allow focal illumination of a single cell or a few cells of choice. Light flash duration will again be controlled by a laser shutter located in front of the beam launcher.

Monitoring Induced EGFP Expression. Long-term monitoring of induced EGFP expression will be by imaging microscopy. To excite fluorescence, the "flashed" cells will be illuminated by light from a monochromator (Polychrome II, TILL Photonics). Cellular fluorescence will be imaged with a cooled CCD camera with good detection quantum efficiency (~0.5) in the green part of the spectrum where EGFP emits (SenSys, Photometrics). Images will be acquired at suitable intervals to give a time course of expression. Image acquisition and analysis will be performed through MetaFluor software (Universal Imaging).

Testing the Utility of Caged NSE in 2-Photon Photolysis. While UV light has been used successfully for photolysis in tissue preparations such as brain slices (for example, see Roerig and Kao, 1999), it is ultimately not ideal for thick, multicellular preparations. Light penetration through a thick specimen is limited by scattering, which is inversely proportional to wavelength to the fourth power (i.e. scattering$\alpha \lambda^{-4}$). Therefore, the shorter the wavelength, the more severely light is scattered by the sample, and the lower the penetration of light into the sample. In two-photon excitation (first reported use in microscopy: Williams et al. 1994), two photons, each at one-half the UV photon energy (and thus twice the wavelength), are "simultaneously" absorbed (in <$10^{-15}$ s) by a molecule. This allows a photolabile molecule to acquire sufficient energy to undergo photolysis. Because of the $\lambda^{-4}$ dependence, doubling the wavelength means that scattering will be attenuated 16-fold. Thus, improved access to the sample interior by the excitation light beam is one major advantage of two-photon excitation. The only technical requirement is that the long-wavelength light be intense enough to allow two photons to be simultaneously captured by a molecule. This requirement is met when short (<$10^{-12}$ s) intense light pulses from solid-state lasers are focused down to small volumes. A second advantage of two-photon excitation is that of true "focal" excitation. Photons within a UV beam are individually at the UV energy regardless of the degree of focus of the beam-focusing merely increases the density of UV photons within a volume. Therefore, individual photons within a UV beam are capable of causing photorelease whether the beam is focused or not. That is, photolysis can, and does, occur in the sample within the entrance and exit light cones on either side of the plane of focus. In two-photon excitation, because the absorbing molecules can capture two photons simultaneously only where the long-wavelength light is the most intense (absorption $\alpha$ (intensity)$^2$), namely within the focal volume of the beam, photolysis occurs exclusively within the focal volume. Elsewhere in the sample, the beam intensity drops off rapidly with distance, and the (intensity)$^2$ dependence prevents any two-photon excitation from occurring. Outside the focal volume, the sample only sees low-energy red light. The two advantages above make two-photon excitation desirable.

We will test the usefulness of BcmNB-NSE-1 in two-photon-induced photorelease. 3T3-ER/EGFP cells will be loaded with caged NSE. The experiments will be performed on a Zeiss LSM510 laser scanning microscope equipped with a Ti-sapphire laser (Mira 900-F, Coherent) for two-photon excitation (tunable from 710 nm to 1000 nm). Photorelease of NSE will be done in two-photon mode, while monitoring of EGFP expression will be through the normal confocal scanning mode of the microscope with 488-nm argon ion laser excitation (Omnichrome). Because optical resolution is of little importance in the detection of intracellular EGFP expression, the confocal pinhole size will be increased to maximize fluorescence signal.

LITERATURE CITED

Aarhus, R., K. Gee, and H. C. Lee. 1995. Caged cyclic ADP-ribose. Synthesis and use. *J. Biol. Chem.* 270:7745–9.

Adams, S. R., J. P. Y. Kao, and R. Y. Tsien. 1988. Biologically useful chelators that release Ca$^{2+}$ upon illumination. *J. Am. Chem. Soc.* 110:3212–3220.

Adams, S. R., J. P. Y. Kao, and R. Y. Tsien. 1989. Biologically useful chelators that take up Ca upon illumination. *J. Am. Chem. Soc.* 111:7957–7968.

Archer, T. K., H. -L. Lee, M. G. Cordingley, J. S. Mymryk, G. Fragoso, D. S. Berard, and G. G. L. Hager. 1994. Differential steroid hormone induction of transcription from the mouse mammary tumor virus promoter. *Molec. Endocrinology* 8:568–576.

Ashburner, M., C. Chihara, P. Meltzer, and G. Richards. 1974. Temporal control of puffing activity in polytene chromosomes. *Cold Spring Harbor Symp. Quant. Biol.* 38:655–662.

Baron, U., M. Gossen, and H. Bujard. 1997. Tetracycline-controlled transcription in eukaryotes: novel transactivators with graded transactivation potential. *Nucl. Acids Res.* 25:2723–2729.

Burcin, M. M., G. Schiedner, S. Kochanek, S. Y. Tsai, and B. W. O'Malley. 1999. Adenovirus-mediated regulable target gene expression in vivo. *Proc. Natl. Acad. Sci. USA* 96:355–360.

Chen, H., R. J. Lin, W. Xie, D. Wilpitz, and R. M. Evans. 1999. Regulation of hormone-induced histone hyperacetylation and gene activation via acetylation of an acetylase. *Cell* 98:675–686.

Cifuente, F., J. Vergara, and C. Hidalgo. 2000. Sodium/calcium exchange in amphibian skeletal muscle fibers and isolated transverse tubules. *Am. J. Physiol.* 279:C89–C97.

Clackson, T., W. Yang, L. W. Rozamus, M. Hatada, J. F. Amara, C. T. Rollins, L. F. Stevenson, S. R. Magar, S. A. Wood, N. L. Courage, X. Lu, F. Cerasoi, Jr., M. Gilman, and D. A. Holt. 1998. Redesigning an FKBP-ligand interface to generate chemical dimerizers with novel specificity. *Proc. Nail. Acad. Sci. USA* 95:10437–10442.

DelPrincipe, F., M. Egger, and E. Niggli. 1999. Calcium signaling in cardiac muscle: refractoriness revealed by coherent activation. *Nat. Cell Biol.* 1:323–329.

Dhadialla, T. S., G. R. Carlson, and D. P. Le. 1998. New insecticides with ecdysteroidal and juvenile hormone activity. *Annu. Rev. Entomol.* 43:545–569.

Ellis-Davies, G. C. R. and J. H. Kaplan. 1988. A new dass of photolabile chelators for the rapid release of divalent cations: Generation of caged Ca and caged Mg. *J. Org. Chem.* 53:1966–1969.

Gee, K. R., L. Niu, K. Schaper, V. Jayaraman, and G. P. Hess. 1999. Synthesis and photochemistry of a photolabile precursor of N-methyl-D-aspartate (NMDA) that is photolyzed in the microsecond time region and is suitable for chemical kinetic investigations of the NMDA receptor. *Biochemistry* 38:3140–3147.

Gossen, M., and H. Bujard. 1992. Tight control of gene expression in mammalian cells by tetracydine-responsive promoters. *Proc. Natl. Acad. Sci. USA* 89:5547–5551.

Gossen, M., S. Freundlieb, G. Bender, G. Müller, W. Hillen, and H. Bujard. 1995. Trascriptional activation by tetracydines in mammalian cells. *Science* 268:1766–1769.

Hagen, V., C. Dzeja, S. Frings, J. Bendig, E. Krause, and U. B. Kaupp. 1996. Caged compounds of hydrolysis-resistant analogues of cAMP and cGMP: Synthesis and application to cyclic nucleotide-gated channels. *Biochemistry*. 35:7762–7771.

Harootunian, A. T., J. P. Y. Kao, S. Paranjape, S. R. Adams, B. V. L. Potter, and R. Y. Tsien. 1991. Cytosolic Ca$^{2+}$ oscillations in REF52 fibroblasts: Ca$^{2+}$-stimulated IP$_3$ production or voltage-dependent Ca$^{2+}$ channels as key positive feedback elements. *Cell Calc.* 12:153–164.

Ho, M. -Y., J. P. Y. Kao, and K. Gregerson. 1995. Dopamine withdrawal elicits prolonged calcium rise to support prolactin rebound release. *Endocrinology* 137:3513–3521.

Holt, J. R., D. C. Johns, S. Wang, Z. Y. Chen, R. J. Dunn, E. Marban, and D. P. Corey. 1999. Functional expression of exogenous proteins in mammalian sensory hair cells infected with vectors. *J. Neurophysiol.* 81:1881–1888.

Hoppe, U. C., E. Marban, and D. C. Johns. 2000a. Molecular dissection of cardiac repolarization by in vivo Kv4.3 gene transfer. *J. Clin. Invest.* 105:1077–1084.

Hoppe, U. C., E. Marban, and D. C. Johns. 2000b. Adenovirus-mediated inducible gene expression in vivo by hybrid ecdysone receptor. *Mol. Ther.* 1:159–164.

Iley, J., R. Moreira, T. Calheiros, and E. Mendes. 1997. Acyloxymethyl as a drug protecting group: Part 4. The hydrolysis of tertiary amidomethyl ester prodrugs of carboxylic acid agents. *Pharm. Res.* 14:1634–1639.

Johns, D. C., R. Marx, R. E. Mains, B. O'Rourke, and E. Marban. 1999. Inducible genetic suppression of neuronal excitability. *J. Neurosci.* 19:1691–1697.

Kang, S. H., and C. Y. Hong. 1987. Simple synthetic routes to geiparvarin. *Tetrahedron Lett.* 28:675–678.

Kao, J. P. Y., A. T. Harootunian, and R. Y. Tsien. 1989. Photochemically generated cytosolic calcium pulses and their detection by fluo-3. *J. Biol. Chem.* 264:8179–8184.

Kao, J. P. Y., and S. R. Adams. 1993. Photosensitive caged compounds: design, properties, and applications. In "Optical Microscopy: Emerging Methods and Applications". B. Herman and J. J. Lemasters, eds. Academic Press.

Kao, J. P. Y., and P. F. Keitz. 1997. "Photosensitive organic compounds that release carbon monoxide upon illumination," U.S. Pat. No. 5,670,664.

Kaplan, J. H., B. Forbush, III, and J. F. Hoffman. 1978. Rapid photolytic release of adenosine-5'-triphosphate from a protected analogue: Utilization by the Na:K pump of human red blood cell ghosts. *Biochemistry* 17:1929–1935.

Lan, A. J. Y., R. O. Heuckeroth, and P. S. Mariano. 1987. Electron-transfer-induced photocyclization reactions of arene-iminium salt systems. Effects of cation diradical deprotonation and desilylation on the nature and efficiencies of reaction pathways followed. *J. Am. Chem. Soc.* 109:2738–2745.

Uopis, J., S. Westin, M. Ricote, Z. Wang, C. Y. Cho, R. Kurokawa, T. -M. Mullen, D. W. Rose, M. G. Rosenfeld, R. Y. Tsien, and C. K. Glass. 2000. Ligand-dependent interactions of coactivators steroid receptor coactivator-1 and peroxisome proliferator-activated receptor binding protein with nuclear hormone receptors can be imaged in live cells and are required for transcription. *Proc. Natl. Acad. Sci. USA* 97:4363–4368.

Makings, L. and R. Y. Tsien. 1994. Caged nitric oxide. Stable organic molecules from which nitric oxide can be photoreleased. *J. Biol. Chem.* 269:6282–6285.

Meyers, A. I., D. L. Temple, D. Haidukewych, and E. D. Mihelich. 1974. Oxazolines. XI. Synthesis of functionalized aromatic and aliphatic acids. A useful protecting group for carboxylic acids against Grignard and hydride reagents. *J. Org. Chem.* 39:2787–2793.

Meyers, A. I., and E. D. Mihelich. 1975. Oxazolines. XXII. Nucleophilic aromatic substitutions on aryl oxazoiines. An efficient approach to unsymmetrically substituted biphenyls and o-alkyl benzoic acids. *J. Am. Chem. Soc.* 97:7383–7385.

Milbum, T., N. Matsubara, A. P. Billington, J. B. Udgaonkar, J. W. Walker, B. K. Carpenter, W. W. Webb, J. Marque, W. Denk, J. A. McCray, and G. P. Hess. 1989. Synthesis, photochemistry, and biological activity of a caged photolabile acetylcholine receptor ligand. *Biochemistry* 28:49–55.

Molin, M., M. C. Shoshan, K. Öhman-Forslund, S. Linder, and G. Akusjärvi. 1998. Two novel adenovirus vector systems permitting regulated protein expression in gene transfer experiments. *J. Virol.* 72:8358–8361.

Muralidharan, S., G. M. Maher, W. A. Boyle, and J. M. Nerbonne. 1993. Caged phenylephrine: Development and application to probe the mechanism of $\alpha$-receptor mediated vasoconstriction. *Proc. Natl. Acad. Sci. U.S.A.* 90:5199.

Niemi, R., P. Turhanen, J. Vepsalainen, H. Taipale, and T. Jarvinen. 2000. Bisphosphonate prodrugs: synthesis and in vitro evaluation of alkyl and acyloxymethyl esters of etidronic acid as bioreversible prodrugs of etidronate. *Eur. J. Pharm. Sci.* 11:173–180.

No, D., T. -P. Yao, and R. M. Evans. 1996. Ecdysone-inducible gene expression in mammalian cells and transgenic mice. *Proc. Natl. Acad. Sci. USA* 93:3346–3351.

Oikawa, N., Y. Nakagawa, K. Nishimura, T. Ueno, and T. Fujita. 1994a. Quantitative structure-activity analysis of larvicidal 1-(substituted benzoyl)-2-benzoyl-1-tert-butylhydrazines against *Chilo suppressalis*. *Pestici. Sci.* 41:139–148.

Oikawa, N., Y. Nakagawa, K. Nishimura, T. Ueno, and T. Fujita. 1994b. Quantitative structure-activity studies of insect growth regulators. *Pestici. Biochem. Physiol.* 48:135–144.

Olah, G. A., and S. J. Kuhn. 1962. Aromatic substitution XII. Steric effects in nitronium salt nitrations of alkylbenzenes and halobenzenes. *J. Am. Chem. Soc.* 84:3684–3687.

Olah, G. A., S. J. Kuhn, S. H. Flood, and J. C. Evans. 1962. Aromatic substitution XIII. Comparison of nitric acid and mixed acid nitrations of alkylbenzenes and benzene with nitronium salt nitrations. *J. Am. Chem. Soc.* 84:3687–3693.

Otti, J., D. Gabriel, and G. Marriott. 1998. Preparation and photoactivation of caged fluorophores and caged proteins using a new class of heterobifunctional, photocleavable crosslinking reagents. *Bioconj. Chem.* 9:143–151.

Perez-Garcia, M. T., J. R. Lopez-Lopez, A. M. Riesco, U. C. Hoppe, e. Marban, C. Gonzalez, and D. C. Johns. 2000. Viral gene transfer of dominant-negative Kv4 construct suppresses an $O_2$-sensitive $K^+$ current in chemoreceptor cells. *J. Neurosci.* 20:5689–5695.

Pittius, C. W., L. Hennighausen, E. Lee, H. Westphal, E. Nicols, J. Vitale, and K. Gordon. 1988. A milk protein gene promoter directs the expression of human plasminogen activator cDNA to the mammary gland in transgenic mice. *Proc. Natl. Acad. Sci. USA* 85:5874–5878.

Pollack, R., and V. M. Rivera. 1999. Regulation of gene expression with synthetic dimerizers. *Meth. Enzymol.* 306:263–281.

Robinson, G. W., R. A. McKnight, G. H. Smith, and L. Hennighausen. 1995. Mammary epithelial cells undergo secretory differentiation in cycling virgins but require pregnancy for the establishment of terminal differentiation. *Development* 121:2079–2090.

Roerig, B., and J. P. Y. Kao. 1999. Organization of intracortical circuits in relation to direction preference maps in ferret visual cortex. *J. Neurosci.* 19:RC44(1–5).

Rossi, F. M., and J. P. Y. Kao. 1997. Nmoc-DBHQ: A new caged molecule for modulating sarco-plasmic/endoplasmic reticulum $Ca^{2+}$ ATPase activity with light flashes. *J. Biol. Chem.* 272:3266–3271.

Rossi, F. M., M. Margulis, C.-M. Tang, and J. P. Y. Kao. 1997. N-Nmoc-glutamate: A new caged glutamate with high chemical stability and low pre-photolysis activity. *J. Biol. Chem.* 272:32933–32939.

Salerno, C. P., D. Magde, and A. P. Patron. 2000. Enzymatic synthesis of caged NADP cofactors: aqueous NADP photorelease and optical properties. *J. Org. Chem.* 65:3971–3981.

Shang, Y., X. Hu, J. DiRenzo, M. A. Lazar, and M. Brown. 2000. Cofactor dynamics and sufficiency in estrogen receptor-regulated transcription. *Cell* 103:843–852.

Shimizu, B., Y. Nakagawa, K. Hattor, K. Nishimura, N. Kurihara, and T. Ueno. 1997. Molting hormone and larvicidal activities of aliphatic acyl analogs of dibenzoylhydrazine insecticides. *Steroids* 62:638–642.

Suhr, S. T., E. B. Gd, M. C. Senut, and F. H. Gage. 1998. High level transactivation by a modified Bombyx ecdysone receptor in mammalian cells without exogenous retinoid X receptor. *Proc. Nail. Acad. Sci.* 95:7999–8004.

Thomas, H. E., H. G. Stunnenberg, and A. F. Stewart. Heterodimerization of the Drosophila ecdysone receptor with retinoid x receptor and utraspiracle. *Nature* 362:471–475.

Tsai, S. Y., B. W. O'Malley, F. J. DeMayo, Y. Wang, and S. S. Chua. 1998. A novel RU486 inducible system for the activation and repression of genes. *Adv. Drug Deliv. Rev.* 30:23–31.

Tsien, J. Z., D. F. Chen, D. Gerber, C. Tom, E. H. Mercer, D. J. Anderson, M. Mayford, E. R. Kandel, and S. Tonegawa. 1996. Subregion- and cell type-restricted gene knockout in mouse brain. *Cell* 87:1317–1326.

Tsien, R. Y. 1981. A non-disruptive technique for loading calcium buffers and indicators into cells. *Nature* 290:527–528.

Ucker, D. S., and K. R. Yamamoto. 1984. Early events in the stimulation of mammary tumor virus RNA synthesis by glucocorticoids. *J. Biol. Chem.* 12:7416–7420.

Walker, J. W., A. V. Somlyo, Y. E. Goldman, A. P. Somlyo, and D. R. Trentham. 1987. Kinetics of smooth and skeletal muscle activation by laser pulse photolysis of caged inositol 1,4,5-trisphosphate. *Nature* 327:249–252.

Wang, Y., B. W. O'Malley, Jr., S. Y. Tsai, and B. W. O'Malley. 1994. A regulatory system for use in gene transfer. *Proc. Natl. Acad. Sci. USA* 91:8180–8184.

Wang, Y., S. Y. Tsai, and B. W. O'Malley. 1999. Antiprogestin regulable gene switch for induction of gene expression in vivo. *Meth. Enzymol.* 306:281–294.

Wieboldt, R., K. R. Gee, L. Niu, D. Ramesh, B. K. Carpenter, and G. P. Hess. 1994a. Photolabile precursors of glutamate: synthesis, photochemical properties, and activation of glutamate receptors on a microsecond time scale. *Proc. Natl. Acad. Sci. U.S.A.* 91:8752–8756.

Wieboldt, R., D. Ramesh, B. K. Carpenter, and G. P. Hess. 1994b. Synthesis and photochemistry of photolabile derivatives of γ-aminobutyric acid for chemical kinetic investigations of the γ-aminobutyric acid receptor in the millisecond range. *Biochemistry* 33:1526–1533.

Williams, R. M., D. W. Piston, and W. W. Webb. 1994. Two-photon molecular excitation provides intrinsic 3-dimensional resolution for laser-based microscopy and microphotochemistry. *FASEB J.* 8:804–813.

Yao, T. P., W. A. Seagraves, A. E. Oro, M. McKeown, and R. M. Evans. 1992. Drosophila ultraspiracle modulates ecdysone receptor function via heterodimer formation. *Cell* 71:63–72.

Yao, T. P., B. M. Forman, Z. Jiang, L. Cherbas, J. D. Chen, M. McKeown, P. Cherbas, and R. M. Evans. 1993. Functional ecdysone receptor is the product of EcR and Ultraspiracle genes. *Nature* 366:476–479.

Yrjanheikki, J., R. Keinanen, M. Pellikka, T. Hokfelt, and J. Koistinaho. 1998. Tetracyclines inhibit microglial activation and are neuroprotective in global brain ischemia. *Proc. Nail. Acad. Sci. USA* 95:15769–15774.

Zaret, K. S., and K. R. Yamamoto. 1984. Reversible and persistent changes in chromatin structure accompany activation of a glucocorticoid-dependent enhancer element. *Cell* 38:29–38.

What is claimed:

1. A caged non-steroidal ecdysome memetic (NSE) compound represented by the following formula (I, II or III):

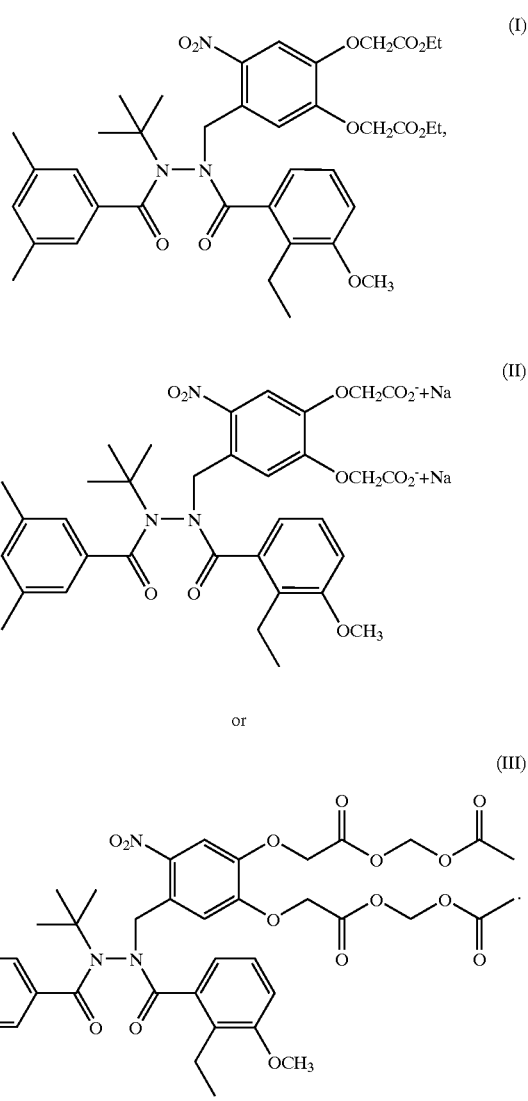

2. The compound of claim 1, wherein said compound is present in an aqueous solution at a concentration of about $10^{-5}$ to $10^{-1}$ M.

3. The compound of claim 2, wherein said aqueous solution has a pH of about 6 to 8.

4. A method for producing a free NSE comprising the step of UV irradiating a compound represented by the following formula (I, II or III):

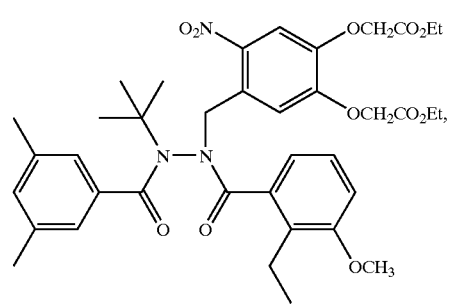

(I)

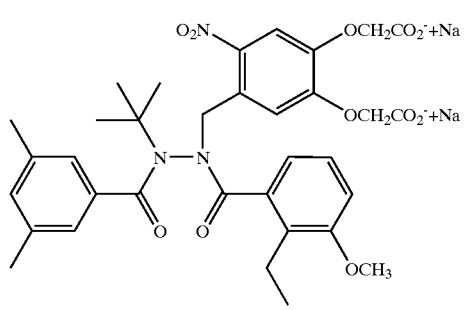

(II)

or

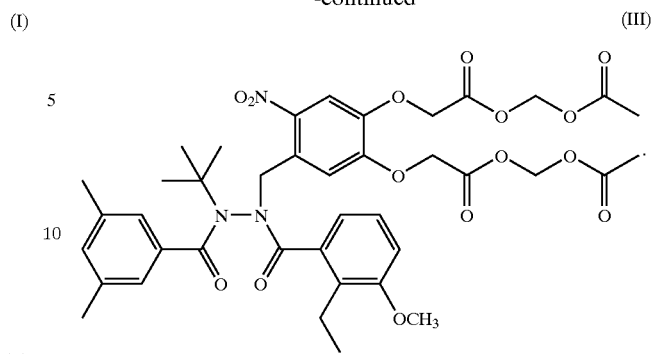

(III)

5. The method of claim 4, wherein said irradiating is carried out at a wavelength of about 300 to 400 nm.

6. The method of claim 4, wherein said irradiating is carried out at about 10° to 40° C.

7. The method of claim 4, wherein said compound is present in an aqueous solution at a concentration of about $10^{-5}$ to $10^{-1}$ M.

8. The method of claim 7, wherein said aqueous solution has a pH of about 6 to 8.

9. The method of claim 4, wherein said irradiating is carried out after perfusing tissue or cultured cells with an aqueous solution containing said compound.

10. The method of claim 4, wherein said irradiating is carried out after microinjecting a cells with an aqueous solution containing said compound.

* * * * *